United States Patent
Nagae

(10) Patent No.: US 9,146,305 B2
(45) Date of Patent: Sep. 29, 2015

(54) SUBJECT INFORMATION ACQUIRING APPARATUS AND SUBJECT INFORMATION ACQUIRING METHOD

(75) Inventor: Kenichi Nagae, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 172 days.

(21) Appl. No.: 13/821,548

(22) PCT Filed: Sep. 8, 2011

(86) PCT No.: PCT/JP2011/005039
§ 371 (c)(1),
(2), (4) Date: Mar. 7, 2013

(87) PCT Pub. No.: WO2012/035723
PCT Pub. Date: Mar. 22, 2012

(65) Prior Publication Data
US 2013/0165791 A1   Jun. 27, 2013

(30) Foreign Application Priority Data
Sep. 16, 2010   (JP) .................................. 2010-207894

(51) Int. Cl.
*A61B 8/00* (2006.01)
*G01S 7/52* (2006.01)
*G01S 15/89* (2006.01)

(52) U.S. Cl.
CPC ............ *G01S 7/52047* (2013.01); *A61B 8/4444* (2013.01); *G01S 15/8915* (2013.01); *G01S 15/8977* (2013.01); *G01S 15/8945* (2013.01); *G01S 15/8993* (2013.01)

(58) Field of Classification Search
CPC .............. A61B 8/4444; G01S 15/8915; G01S 15/8945; G01S 15/8977; G01S 15/8993

USPC ..................... 600/407, 447, 462; 73/623, 626
See application file for complete search history.

(56) References Cited

U.S. PATENT DOCUMENTS 6,155,704 A * 12/2000 Hunt et al. ................... 342/25 F
6,719,696 B2   4/2004 Stergiopoulos et al.
(Continued)

FOREIGN PATENT DOCUMENTS

| CN | 101352354 A | 1/2009 |
|---|---|---|
| JP | 7-077569 A | 3/1995 |

(Continued)

OTHER PUBLICATIONS

A. Dhanantwari et al., "Adaptive 3D Beamforming for Ultrasound Systems Deploying Linear and Planar Phased Array Probes," 2003 IEEE Ultrasonics Symposium, vol. 2, Oct. 15, 2003, pp. 1855-1858.

(Continued)

*Primary Examiner* — Baisakhi Roy
(74) *Attorney, Agent, or Firm* — Canon USA, Inc. IP Division

(57) ABSTRACT

A subject information acquiring apparatus of the present invention includes a probe which has a plurality of elements arranged in an array which receive elastic waves propagating within a subject and converts the received elastic waves to a received signals, a first signal processing unit which uses the received signals output by the elements to calculate a first output signal corresponding to the elastic waves from a target position, a second signal processing unit which uses the first output signal for the target position to calculate a second output signal corresponding to elastic waves from the target position, and an image processing unit which uses the second output signal to generate image data for display. In this case, at least one of the first signal processing unit and the second signal processing unit uses adaptive signal processing to calculate the first output signal or the second output signal.

12 Claims, 8 Drawing Sheets

(56) References Cited

U.S. PATENT DOCUMENTS

| | | | |
|---|---|---|---|
| 7,239,263 B1* | 7/2007 | Sawa | 342/25 F |
| 7,581,446 B2* | 9/2009 | Troxler | 73/623 |
| 8,726,734 B1* | 5/2014 | Lin | 73/626 |
| 2008/0052583 A1 | 2/2008 | Matteson et al. | |
| 2008/0146937 A1* | 6/2008 | Lee et al. | 600/462 |
| 2009/0043209 A1 | 2/2009 | Hirama | |

FOREIGN PATENT DOCUMENTS

| | | |
|---|---|---|
| JP | H07-236642 A | 9/1995 |
| JP | H07-327986 A | 12/1995 |
| JP | H11-155858 A | 6/1999 |
| JP | 2001-187055 A | 7/2001 |
| JP | 2004-317240 A | 11/2004 |
| JP | 2006-121513 A | 5/2006 |
| JP | 2009-028366 A | 2/2009 |
| JP | 2010-183979 A | 8/2010 |
| RU | 2249179 C1 | 3/2005 |
| WO | 2010/100868 A1 | 9/2010 |

OTHER PUBLICATIONS

M. Sasso et al., "Medical Ultrasound Imaging Using the Fully Adaptive Beamformer," 2005 IEEE International Conference on Acoustics, Mar. 18, 2005, pp. 489-492.

JF. Synnevag et al., "Benefits of Minimum-Variance Beamforming in Medical Ultrasound Imaging," IEEE Transactions on Ultrasonics, Ferroelectrics, and Frequency Control, vol. 56, No. 9, Sep. 1, 2009, pp. 1868-1879.

* cited by examiner

SUBJECT INFORMATION ACQUIRING APPARATUS AND SUBJECT INFORMATION ACQUIRING METHOD

TECHNICAL FIELD

The present invention relates to subject information acquiring apparatuses. In particular, it relates to a subject information acquiring apparatus which receives elastic waves and acquires subject information as image data.

BACKGROUND ART

An apparatus has been known which diagnoses a breast cancer by transmitting ultrasound that is elastic waves, receives waves reflected by an internal part of a subject and acquires an ultrasonic echo image. PTL 1 discloses a method which mechanically scanning a probe having elements that exchange ultrasound one-dimensionally and generates three-dimensional image data.

On the other hand, adaptive signal processing has been developed in a radar field, for example. Constrained Minimization of Power (CMP) which is one method of adaptive signal processing which minimizes the signal power when radio waves are received with a plurality of elements by fixing the sensitivity for one direction. According to the adaptive signal processing, the processing parameter is adaptively changed direction by direction. This kind of adaptive signal processing method advantageously may improve the spatial resolution, particularly, the resolution in orientation direction. NPL 1 discloses a method which uses such an adaptive signal processing method to generate ultrasonic echo image data for a higher resolution.

Processing to be performed when adaptive signal processing is applied to an ultrasonic received signal will be described on the basis of CMP, for example. First of all, the processing will be described up to calculation of a correlation matrix from a received signal. Hilbert transform, that is, delay processing circuit according to a target position is first performed on received signals output from a plurality of elements. A complex-represented received signal is thus acquired. When the sth sample of signals acquired by processing a received signal from the kth element is $x_k[s]$, the input vector $X[s]$ of the sth sample may be defined as:

$$X[s] = [x_1[s], x_2[s], \ldots, x_M[s]]^T \quad \text{[Math.1]}$$

where M is the number of elements.

The input vector $X[s]$ is used to calculate a correlation matrix Rxx.

$$R_{xx} = E[X[s]X^H[s]] \quad \text{[Math.2]}$$
$$= \begin{bmatrix} E[x_1[s]x_1^*[s]] & E[x_1[s]x_2^*[s]] & \ldots & E[x_1[s]x_M^*[s]] \\ E[x_2[s]x_1^*[s]] & E[x_2[s]x_2^*[s]] & \ldots & E[x_2[s]x_M^*[s]] \\ \vdots & \vdots & \ddots & \vdots \\ E[x_M[s]x_1^*[s]] & E[x_M[s]x_2^*[s]] & \ldots & E[x_M[s]x_M^*[s]] \end{bmatrix}$$

The "H" at the right shoulder in the expression indicates a complex conjugate transposition, and "*" at the right shoulder indicates a complex conjugate. E[ ] expresses processing of calculating a time average and means that the sample number ("s" here) is changed to calculate the average.

Next, in order to prevent the influence by correlated interference waves that reach from a position excluding a target position to a probe, a space average method is applied to the correlation matrix Rxx to acquire the average correlation matrix R'xx.

$$R'_{xx} = \sum_{n=1}^{M-K+1} z_n R_{xx}^n \quad \text{[Math.3]}$$

R"xx indicates a submatrix of the correlation matrix Rxx and moves on a diagonal component of Rxx. R"xx has a K*K size with the (n,n) component of Rxx as the first diagonal component. Zn is a coefficient for calculating a submatrix and is adjusted such that the total sum of Zn may be equal to 1.

According to CMP, a weight for minimizing the output power under a constrained condition is acquired. The weight is a weight represented by a complex vector. When the sensitivity against an ultrasonic received signal from a target position is constrained to 1, the optimum weight Wopt for minimizing the output power may be acquired in CMP by the following expression.

$$W_{opt} = \gamma R'^{-1}_{xx} C, \quad \text{[Math.4]}$$
$$\gamma = \frac{1}{C^H R'^{-1}_{xx} C}$$

C is a constrained vector and changes in accordance with the position of an element and a target position. However, when delay processing circuit is performed on received signals, all values of C may be 1 in the size (K in this case) of the average correlation matrix. The power Pmin calculated by using the weight $W_{opt}$ may be acquired as follows:

$$P_{min} = \frac{1}{2} \frac{1}{C^H R'^{-1}_{xx} C} \quad \text{[Math.5]}$$

In this way, according to CMP, a correlation matrix and even an average correlation matrix are acquired from received signals. The inverse matrix may be used to calculate a weight or the power when a weight is used. The weight or the power when a weight is used is a weight or power when the sensitivity from a target position against an ultrasonic signal is defined to 1 to suppress ultrasonic signals from other positions. In other words, CMP allows selective extraction of an ultrasonic signal from a target position, resulting in a higher spatial resolution. Notably, the power may be calculated by QR decomposition and back substitution processing, instead of direct calculation of the inverse matrix.

CITATION LIST

Patent Literature

PTL 1: Japanese Patent Laid-Open No. 2009-028366
Non Patent Literature
NPL 1: Proc. Acoustics, Speech Signal Process., pp. 489-492 (March 2005)

SUMMARY OF INVENTION

However, the processing size may be a problem when adaptive signal processing is used on a configuration in which one-dimensional or two-dimensional array probe is used to generate three-dimensional image data, for higher spatial resolution.

Adaptive signal processing may require inverse matrix calculation, QR decomposition, eigenvalue calculation or the like on a matrix having a size according to the number of received signals. It has been known that such a calculation size of the processing increases in proportion to the cube of the matrix size. For example, consider the case where one-dimensional array probe which receives signals with a 64-element aperture is moved in the direction that is orthogonal to the array direction to acquire signals for 32 slices and then adaptive signal processing is performed thereon. This case is equivalent to the case where the signals for 64*32=2048 CHs are acquired and processed two-dimensionally at the same time. A large amount of processing may be required for the adaptive signal processing by using the (2048 CH) input signals (received signals), and the processing time and/or the size of circuit may increase.

The present invention was made in view of the aforementioned problems, and the present invention reduces the workload of adaptive signal processing when adaptive signal processing is applied to acquire image data having a high spatial resolution.

A subject information acquiring apparatus of the present invention includes a probe which has a plurality of elements arranged in an array which receive elastic waves propagating within a subject and converts the received elastic waves to a received signals, a first signal processing unit which uses the received signals output by the elements to calculate a first output signal as the signal corresponding to the elastic waves from a target position, a second signal processing unit which uses the first output signal for the target position to calculate a second output signal as the signal corresponding to elastic waves from the target position, and an image processing unit which uses the second output signal to generate image data for display. In this case, at least one of the first signal processing unit and the second signal processing unit uses adaptive signal processing to calculate the first output signal or the second output signal.

A subject information acquiring method of the present invention receives elastic waves propagating within the subject with a plurality of elements, converts the received elastic waves to received signals, and uses the received signals to generate image data, and the method includes a first signal processing step which uses the received signals output by the elements to calculate a first output signal as the signal corresponding to the elastic waves from a target position, a second signal processing step which uses the first output signal for the target position to calculate a second output signal as the signal corresponding to elastic waves from the target position, and an image processing step which uses the second output signal to generate image data for display, wherein at least one of the first signal processing step and the second signal processing step uses adaptive signal processing to calculate the first output signal or the second output signal.

According to the present invention, workload for adaptive signal processing may be reduced when adaptive signal processing is applied to acquire image data having a high spatial resolution.

DESCRIPTION OF EMBODIMENTS

Figure 1:
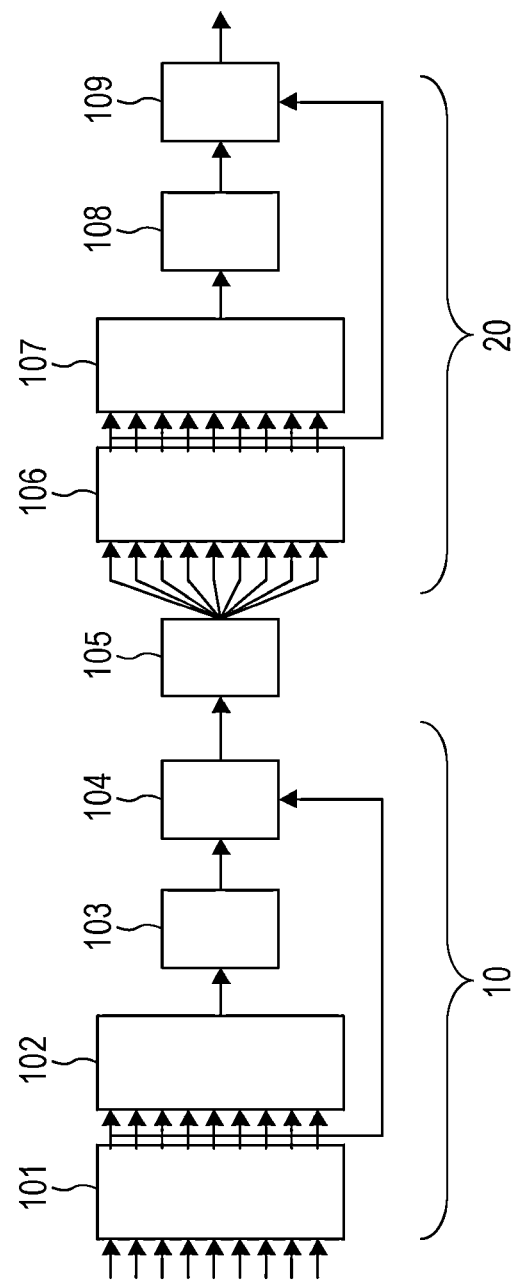
FIG. 1 is schematic system diagram illustrating an outline of signal processing of the present invention.

According to the present invention, the elastic waves include those called sonic waves, ultrasound, acoustic waves, and photoacoustic waves. Elastic waves propagated within a subject are received with a probe. In other words, a subject information acquiring apparatus according to the present invention includes an apparatus using an ultrasonic echo technology which transmits ultrasound to a subject, receives the reflected waves (reflected ultrasound) from the inside of the subject and acquires subject information as image data and an apparatus using an photoacoustic effect which irradiates light (electromagnetic waves) to a subject, receives acoustic waves (typically, ultrasound) occurring within the subject and acquires subject information as image data. According to the former apparatus using the ultrasonic echo technology, the subject information to be acquired is information reflecting differences in acoustic impedance between tissues within the subject. According to the latter apparatus using the photoacoustic effect, the subject information to be acquired is information on a source distribution of acoustic waves caused by light irradiation, an initial pressure distribution within a subject, a light energy absorption density distribution derived from the initial pressure distribution, an absorption coefficient distribution, or a concentration distribution of a substance included in the tissue. The concentration distribution of a substance may be an oxygen saturation distribution, or an oxidized/reduced hemoglobin concentration distribution, for example.

Before describing the outline of a signal processing unit of the present invention and reasons why the processing method works, the processing size will first be examined when all two-dimensionally input received signals are processed by an adaptive signal processing method. The following description is on an example where a probe having a one-dimensional array of a plurality of elements (hereinafter, also called a "one-dimensional array probe") is mechanically scanned in the direction orthogonal to the array direction to acquire received signals two-dimensionally. However, the present invention is also applicable by using a probe having a two-dimensional array of a plurality of elements (hereinafter, also called a "two-dimensional array probe"). In the description on the present invention, the direction in which a probe scans mechanically is called a direction of mechanical scan. The direction orthogonal to the array direction of a probe is called an elevation direction. In the following description, a probe scans in the elevation direction, for example.

When the number of inputs of elements in the array direction is NL, the number of inputs in the elevation direction is NE, the total number of input signals X which are received signals is NL*NE (=Ntotal). The correlation matrix Rxx calculated from X is a matrix having a size of Ntotal*Ntotal. When a space average method is applied to suppress an influence by correlation interference wave and the space average number is half of Ntotal, the average correlation matrix R'xx has a size of (Ntotal/2)*(Ntotal/2). By using the inverse matrix calculated from the average correlation matrix, the corresponding weight or the power using the weight is calculated. In the adaptive signal processing, the step of calculating the inverse matrix occupies a large part of the workload. The workload of the step of calculating the inverse matrix is proportional to the cube of the size (Ntotal/2) of the matrix.

For example, in adaptive signal processing using the number of inputs in the array direction for received signals by 64 elements (NL) and the number of inputs in the elevation direction for received signals for 32 slices (NE), the number of input CHs (Ntotal) is equal to 2048 CH. The size of the matrix for calculating the inverse matrix is equal to 1024*1024, which results in a large processing size and increases the size of circuit.

Outline of Signal Processing

Figure 9:
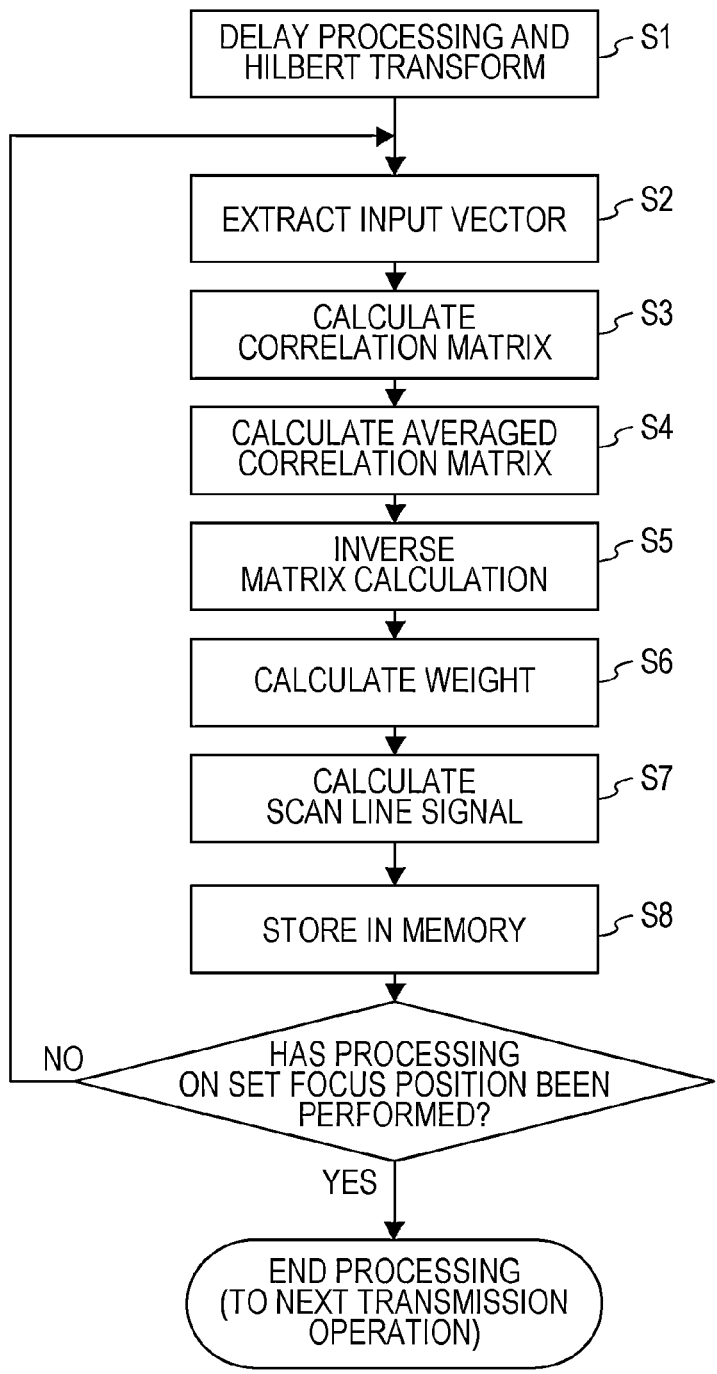
FIG. 9 is a flowchart illustrating a processing flow by a first signal processing unit.

Next, an outline of signal processing of the present invention will be described with reference to FIG. 1 and FIG. 9. It is assumed that both first signal calculating unit and second signal calculating unit apply adaptive signal processing, for example. However, according to the present invention, at least one of the first signal calculating unit and second signal calculating unit may be required to use adaptive signal processing to acquire the effect of a higher spatial resolution. One of the first signal calculating unit and second signal calculating unit may use adaptive signal processing.

In order to measure ultrasonic echo, ultrasound is transmitted to a subject, and the reflected waves is received by one-dimensionally aligned elements. Each of the elements converts the waves to a received signal and outputs it to the first signal calculating unit. A first stage of the processing to be performed on a received signal by the first signal calculating unit 10 will be described below. According to the present invention, a signal corresponding to elastic waves from a target position, which is calculated by the first signal calculating unit, will be called a first output signal.

First Signal Calculating Unit

A delay processing circuit 101 performs delay processing according to a target position on a received signal from an element of a probe (the number of inputs NL) and converts the received signal to a complex signal by Hilbert transform. The complex signal is output as the input vector X[s] of the sth sample (step S1).

Next, an averaged correlation matrix calculating circuit 102 extracts signals for the time average number (such as 10 samples) from input vectors updated at predetermined time intervals (step S2) and calculates the correlation matrix Rxx of the extracted signals (step S3). The partial correlation matrices are averaged to acquire and output the average correlation matrix R'xx (step S4). If the average correlation matrix R'xx is the half size of the correlation matrix Rxx, the size of the output average correlation matrix R'xx is equal to (NL/2)*(NL/2). A weight calculating circuit 103 acquires the inverse matrix of the input average correlation matrix R'xx (step S5) and outputs the weight Wopt (step S6).

A first output calculating circuit 104 uses the input weight Wopt and the input vector used for calculating the correlation matrix to calculate the sth sample's scan line signal y[s] as a first output signal (step S7). The sth sample's scan line signal y[s] is a signal corresponding to ultrasound (reflected wave) from one point (target position) on the transmitted ultrasonic line (scan line). The scan line signal y[s] is stored in a memory 105 (step S8).

The processing from step S2 to step S8 is repeated by changing the target position along the direction of ultrasound transmission (scan line direction) and changing the input vectors to be extracted. Typically, input vectors are extracted from the latest received time. In other words, the calculation of the sth sample's scan line signal y[s] is followed by the calculation of (s+1th sample's scan line signal y[s+1]. Repeating this processing for the number of target positions in the scan line direction provides a scan line signal.

After the processing on the target positions within a preset measurement range (such as a range in the direction of depth of a subject) ends, the processing from step S1 to S8 is performed on a received signal of reflected waves received by the next transmission (such as transmission by the adjacent 64 elements in linear scanning.

Because the input vector X[s] and the weight Wopt have different numbers of signals by the signals used for the space average, a signal X'[s] resulting from the extraction of NL/2 elements at the center of the input vector X[s] is used for the calculation as in the following expression, for example. However, a signal having NL/2 elements resulting from moving average of the input vector X[s].

$$y[s]=W_{opt}^{H}X'[s] \qquad \text{[Math.6]}$$

The weight refers to a weight represented in complex vector. X'[s] is also complex-represented signal. Acquiring an inner product thereof by adaptive signal processing means summing up received signals of CHs (or received signals output from the elements) after changing (adjusting) the phases in accordance with the target positions. In other words, when the weight is changed as the target position is moved, the amount of change in phase on the received signals of the CHs also changes.

Figure 2:
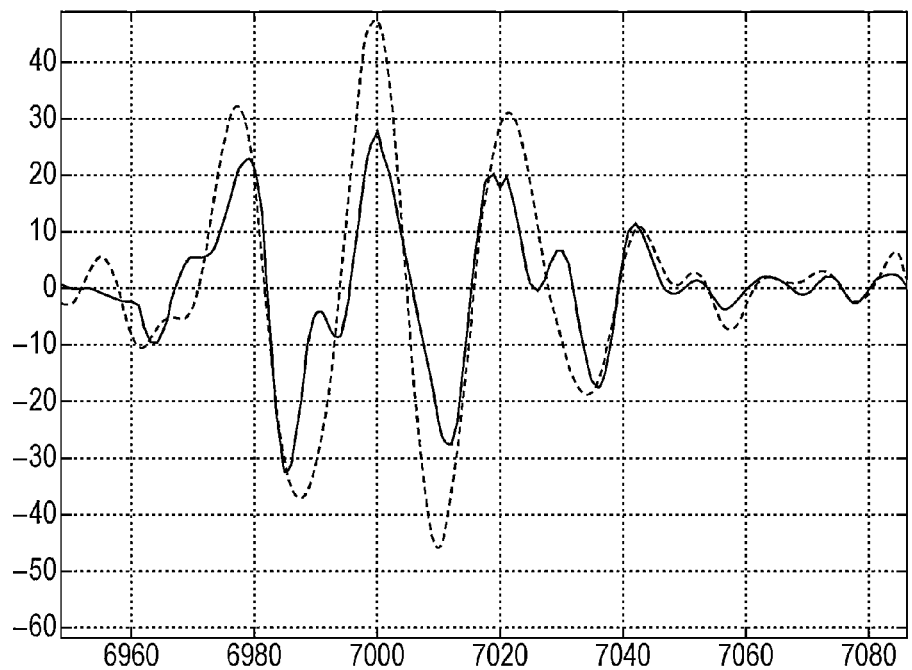
FIG. 2 is a graph illustrating a plot of a signal processed by adaptive signal processing and delay and sum.

FIG. 2 is a graph illustrates a plot of a signal (first output signal) calculated by performing adaptive signal processing on one received signal and a signal calculated by normal delay and sum. In FIG. 2, the solid line indicates a plot of a signal having undergone adaptive signal processing, and the broken line indicates a plot of a signal having undergone delay and sum. The horizontal axis indicates the received sample number, and the vertical axis indicates a value which is dimensionless and is proportional to acoustic pressure. The adaptive signal processing in FIG. 2 recalculates and changes the weight for every 10 samples. Thus, the phases of signal waveforms appear as being displaced and being discontinuous at the position of the sample 7000 and sample 7010.

Second Signal Calculating Unit

Figure 10:
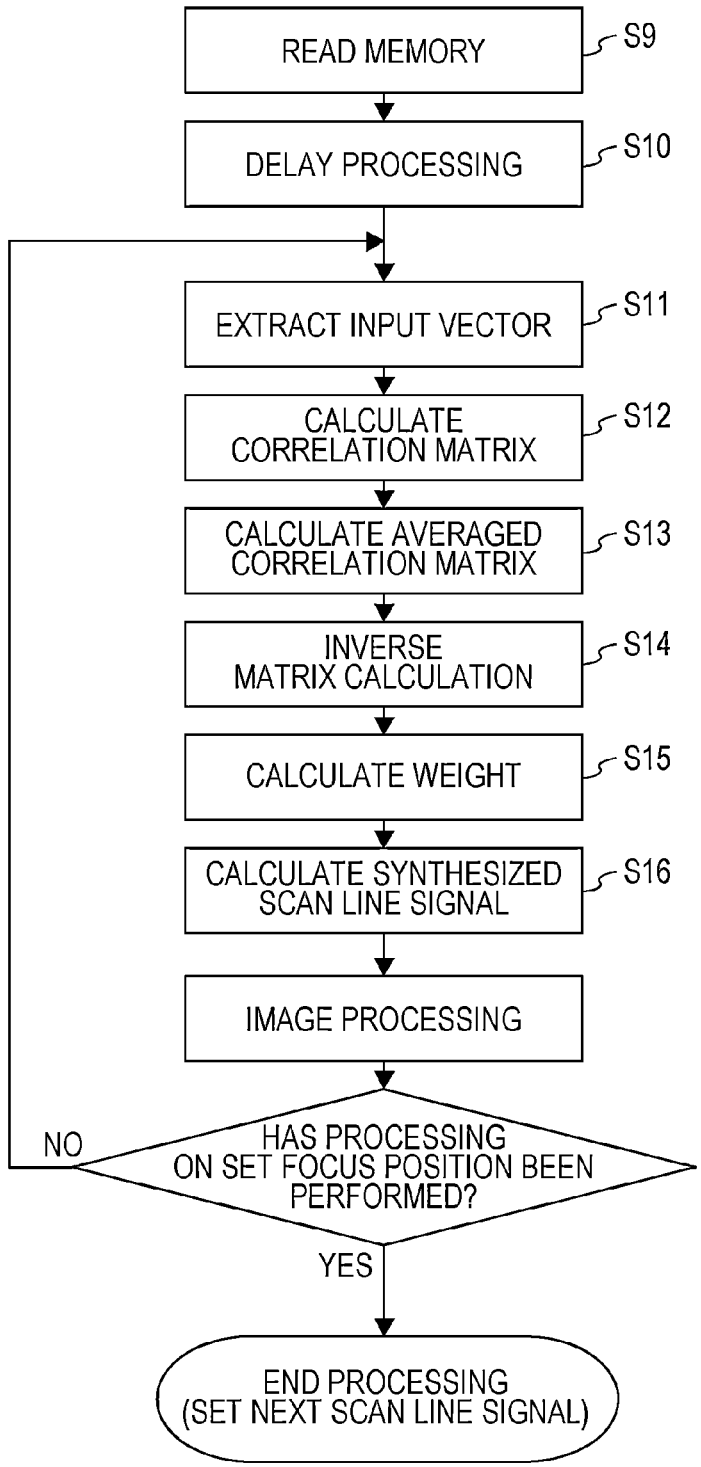
FIG. 10 is a flowchart illustrating a processing flow by a second signal processing unit.

Next, processing by a second signal calculating unit 20 will be described with reference to FIG. 1 and FIG. 10. The second signal calculating unit 20 performs the second stage of the processing on received signals, including performing adaptive signal processing on input signals which are a plurality of scan line signals (first output signals) calculated at different positions by scanning of a probe, for example. According to the present invention, a signal corresponding to elastic waves from a target position, which is calculated by the second signal calculating unit is called a second output signal.

From the memory 105, a plurality of scan line signals along the direction of the elevation of a probe are read (step S9). A delay processing circuit 106 performs delay processing according to the target position on a plurality of scan line signals (the number of inputs: NE) and outputs the first output signal, input vector X[s], calculated by the first signal calculating unit (step S10). If the first signal calculating unit has applied adaptive signal processing, the first input signal is already a complex signal. This eliminates the necessity for new Hilbert transform processing, and the complex signal having undergone the delay processing is directly output as the input vector X[s].

Next, an averaged correlation matrix calculating circuit 107 extracts complex signals for the time average number from input vectors updated at predetermined time intervals (step S11) and calculates the correlation matrix Rxx of the extracted signals (step S12).

The partial correlation matrices are averaged to acquire and output the average correlation matrix R'xx (step S13). If the average correlation matrix R'xx is the half size of the correlation matrix Rxx, the size of the output average correlation matrix R'xx is equal to (NE/2)*(NE/2). A weight calculating circuit 108 acquires the inverse matrix of the input average correlation matrix R'xx (step S14) and calculates and outputs the weight Wopt (step S15).

A second output calculating circuit 109 uses the input weight Wopt and the input vector used for calculating the correlation matrix to calculate a synthesized scan line signal y[s] as the second output signal (step S16). After that, an image processing unit (not illustrated in FIG. 1) uses the synthesized scan line signal to calculate an envelope or perform log compression and generates the resulting subject information as display image data.

In the second-stage signal processing, ultrasound is not transmitted, but the scan line signal (first output signal) which is the output of the signal processing unit in the first stage is used for the processing. In this case, the amount of delay is preferably calculated in the delay processing in the second-stage by the signal processing unit by assuming that ultrasound is transmitted from the positions of the probe where the scan line signals have been calculated to a target position and the reflected waves have been received at the positions of the probe. However, an apparatus using the photoacoustic effect, that is, an apparatus which irradiates light or electromagnetic waves to a subject and performs processing on the resulting acoustic waves (typically, ultrasound) may use the distances between the positions of the probe where the scan line signals have been calculated and a target position to calculate the amount of delay.

The processing from step S11 to step S16 is repeated by changing the target position and changing the input vectors to be extracted. After the processing on the target positions within a preset measurement range ends, the processing from step S9 is performed again by changing the scan line signal to be used.

Reasons why Processing Method Above Works

When the adaptive signal processing is performed also in the second stage as described above, the phases of the scan line signals acquired by the first signal processing unit 10 may be used for the processing. This may require holding the phases of the signals corresponding to ultrasound from a target position included in the scan line signals. Even when simple synthetic aperture processing is performed in the second stage, the phases of the scan line signals may also be used for the processing, which may require holding the phases of the signals corresponding to ultrasound from a target position. In other words, as illustrated in FIG. 2, it may be considered that the signal processing in the second stage does not work with a scan line signal which appears to have the phase displaced in accordance with the update of the weight.

Focusing on a constrained vector C in adaptive signal processing, the phase of the signal corresponding to ultrasound from a target position will be examined again here. CMP is a method for acquiring a weight for minimizing the output power under a constrained condition or the output power. The constrained condition is generally represented by the following expression.

$$C^T W^* = H \quad [\text{Math.7}]$$

In this case, C is a constrained matrix (which defined a target direction, for example), W is a weight to be acquired, and H defined a response vector to the constrained matrix (such as a target direction). Under the constrained condition, the processing for acquiring W which satisfies the following expression is CMP.

$$\min_W \left( P_{out} = \frac{1}{2} W^H R_{xx} W \right) \quad [\text{Math.8}]$$

When one direction or one position is focused as in this case, the calculations may be performed by defining that the response H to a constrained condition is 1 and C is not a matrix but a constrained vector.

$$C^T W^* = 1 \quad [\text{Math.9}]$$

In the expression, C is a vector in complex representation. The weight W is also a vector in complex representation. The fact that the inner product of the vectors is equal to 1, that is, the inner product does not include an imaginary number component provides that the phase does not change even when a signal from the direction or position represented by the constrained vector is multiplied by the weight W.

That is, when received signals in complex representation for CHs are multiplied by a weight represented by a complex number, the phases of the received signals of the CHs are changed. Then they are summed up, the phase of the signal corresponding to ultrasound from a target position represented by a constrained vector is not changed. This means that the phase of the ultrasonic signal from a focus direction or target position is kept held.

In this way, though the phase of a scan line signal appears as not being saved in FIG. 2, the phase of a signal from a target position that is actually necessary is held. For that reason, as in the present invention, the processing method which performs processing using the phase works in the second signal processing unit.

Processing Size

Next, the processing size will be described in a case where a first signal processing unit and second signal processing unit as described above perform adaptive signal processing.

The size of the average correlation matrix is (NL/2)*(NL/2) in the first signal processing unit. The size of the average correlation matrix is (NE/2)*(NE/2) in the second signal processing unit. Because the respective inverse matrices are calculated independently, the total amount of processing is proportional to the cube of the sizes ((NE/2) and (NL/2)).

For example, adaptive signal processing will be described which uses received signals for 64 elements (NL) in the array direction of a one-dimensional array probe and for 32 slices (NE) in the elevation direction. The size of the matrix for calculating the inverse matrix is equal to 32*32 in the first signal processing unit and 16*16 in the second signal processing unit. They are smaller in matrix size than 1024*1024 of the adaptive signal processing to be performed on all of two-dimensional inputs as described above. Because workload for the inverse matrix is proportional to the cube of the matrix size, the ratio between the amounts of processing of the configuration of the present invention and the processing to be performed all of two-dimensional inputs at the same time is $(32^3+16^3):(1024^3)=9:64^3$, which reduces workload to about $1/29000$. Thus, adaptive signal processing is applicable with a reduced processing size. However, according to the present invention, the number of inputs (or the number of NL or NE) for performing adaptive signal processing in the first signal processing unit or second signal processing unit may be a desirable (plurality of) number that is equal to or higher than three. The number of inputs (or the number of NL or NE) for performing delay and sum or synthesized aperture processing in the first signal processing unit or second signal processing unit may be a desirable (plurality of) number that is equal to or higher than two.

Having described the processing method for directly acquiring the inverse matrix, the same effect can be provided by the solution to simultaneous linear equations with the QR decomposition and back substitution processing on the average correlation matrix because workload is proportional to the cube of the matrix size.

Having described above the example that the direction of the mechanical scan of a one-dimensional array probe is normal to the array direction of the probe (scanning in the elevation direction), the direction of the mechanical scan of the present invention may be any direction excluding the direction that is normal to the array direction. The present invention is applicable to the movement of a probe having a high degree of freedom by monitoring the amount and direction of the movement of the probe, grasping the probe positions where scan line signals are calculated, and operating the second signal processing unit by using the positional information.

The number of elements to be arranged in the probe may be any plural number that is equal to or higher than two, and any desirable number of elements may be provided. Further having described the method that scans a one-dimensional probe to acquire ultrasound, the present method is also applicable to the ultrasonic received signals which are simultaneously acquired by a two-dimensional array probe having elements two-dimensionally. The received signals input from the two-dimensional array probe may be divided into two directions of the one-dimensional array direction and the direction that is normal to the one-dimensional array direction, and the first signal processing unit and second signal processing unit may be used for the directions.

Having described above the processing on a received signal acquired by transmitting ultrasound and receiving the reflected waves, the present invention is not limited to the form. For example, the effect of the present invention may be acquired by performing the same processing on a received signal acquired by irradiating light (electromagnetic waves) to a subject and receiving acoustic waves caused by a photoacoustic effect. However, the direction for calculating the first and/or second output signals may be different from the case using an ultrasonic echo. In the case using an ultrasonic echo, the first output signal and/or second output signal are calculated along the scan line direction to acquire the first output signal and/or second output signal on the line (scan line) corresponding to the direction of depth of the subject, as described above. However, in the case using a photoacoustic effect, the first output signal and/or second output signal may be processed in real time by performing the calculation in the direction orthogonal to the direction of depth of the subject. Yet, the signals stored in the memory may be calculated in any order.

In this way, the present invention may reduce the processing size of adaptive signal processing when the adaptive signal processing is applied to acquire image data having a high spatial resolution. With reference to drawings, embodiments of the present invention will be described.

First Embodiment

Figure 3:
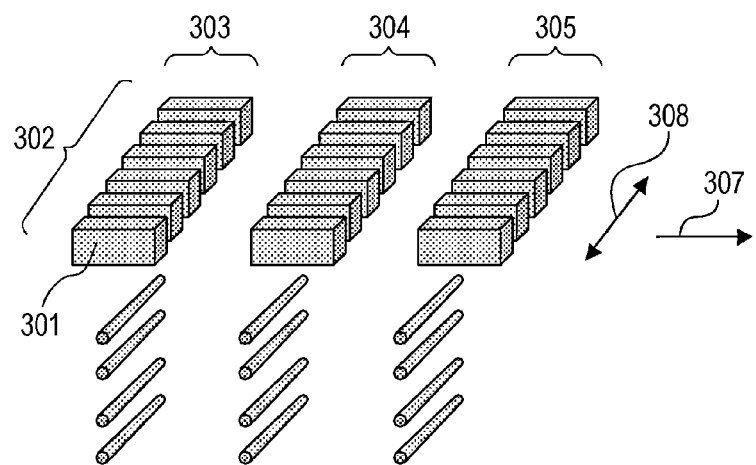
FIG. 3 is a conceptual diagram when a probe mechanically scans.

An apparatus according to this embodiment mechanically scans a one-dimensional array probe and at the same time using delay and sum for a first signal processing unit and adaptive signal processing for a second signal processing unit. FIG. 3 is a conceptual diagram when a probe 302 having a plurality of elements 301 one-dimensionally is mechanically scanned from the position 303 to the position 305. An array direction 308 refers to the direction of the array of the elements 301, and a mechanical scan direction 307 refers to the direction in which the probe 302 is moved by mechanical scan.

Figure 4:
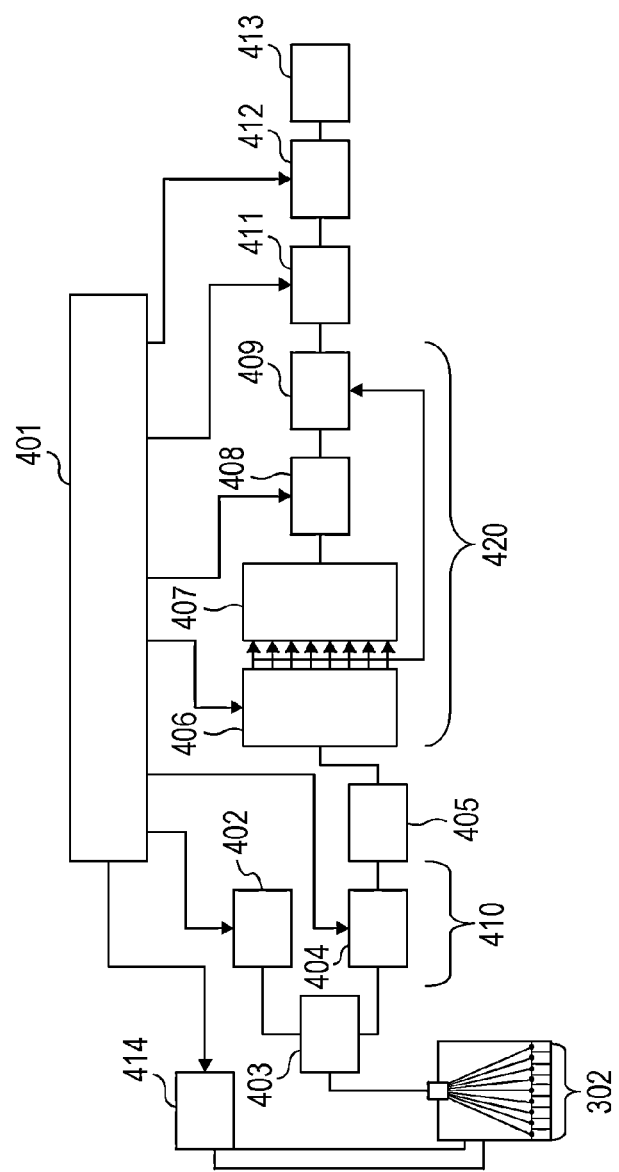
FIG. 4 is a schematic system diagram for describing a first embodiment.

The operation when the probe 302 is at a position 303 will be described with reference to FIG. 4. FIG. 4 is a schematic system diagram of an apparatus using an ultrasonic echo, which is a subject information acquiring apparatus according to this embodiment.

A transmission operation will be described first. Information according to the direction of transmission is input from a system control unit 401 to a transmitting circuit 402. The transmitting circuit 402 calculates a delay time according to the array of elements of the probe and outputs a voltage waveform to the switching circuit 403. The switching circuit 403 selectively connects elements in the part to be used of the probe 302 and the transmitting circuit. For linear scan, for example, serial 64 elements of the array of elements of the 256 CH are selected and connected to the transmitting circuit. Ultrasound is transmitted from the probe 302 to the inside of a subject.

Next, an operation by first signal processing unit will be described. The ultrasound reflected in accordance with the acoustic impedance distribution within the subject is received by an element and is converted to a received signal which is an electric signal. After that, a received signal by each element is input through the switching circuit 403 to a first signal processing unit 410. A delay and sum processing circuit 404 uses the received signal input through the switching circuit 403 and target position information input from the system control unit 401 to perform what-is-called delay and sum in which phases of received signals corresponding to ultrasound from a target position are summed up after delay processing is performed thereon to equalize them. The scan line signal (first output signal) for each target position, which is calculated as described above, is stored in a memory 405.

The transmission and reception cycle is repeated by changing the element 301 to be connected by the switching circuit 403 (for example, by moving the element to be connected one by one in the array direction). The scan line signals calculated by the first signal processing unit 410 are stored in the memory 405.

Figure 5:
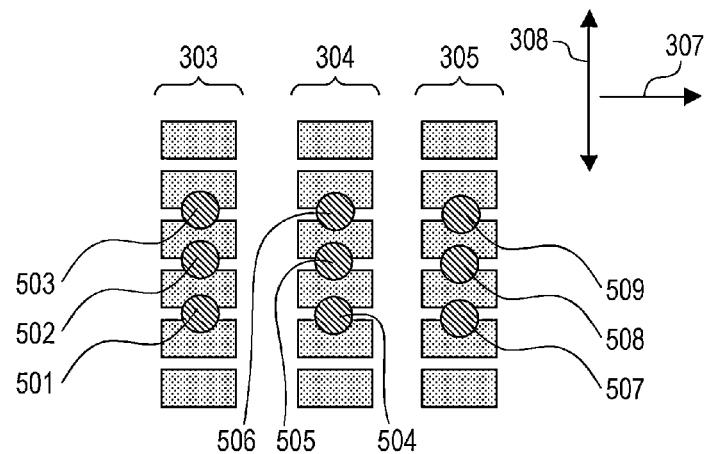
FIG. 5 is a schematic diagram illustrating a relationship between positions of a probe and positions for acquiring scan line signals.

Next, with reference to FIG. 5, the movement of the probe will be described. FIG. 5 corresponds to the top view of FIG. 3 and illustrates a positional relationship between positions of the probe and acquired scan line signals. The system control unit 401 transmits a control signal to a stage control circuit 414 and moves the probe 302 to a position 304. Also at the position 304, scan line signals calculated by the first signal processing unit 410 are stored in the memory 405, similarly at the position 303.

By repeating this operation, three scan line signals (501 to 506) for each of the position 303 and position 304 are acquired as illustrated in FIG. 5. The probe 302 is further moved to a position 305, and the same processing as that at the positions 303 and 304 is performed to calculate the scan line signal 507 and store it in the memory 405.

Referring back to FIG. 4, a flow of a signal in the second signal processing unit will be described. Within the memory 405, the scan line signal 501 through the scan line signal 507 are stored. The scan line signal 501, scan line signal 504, and scan line signal 507 are selected from the scan line signals, and the second signal processing unit 420 performs processing thereon.

A delay processing circuit 406 receives the scan line signal 501, scan line signal 504, and scan line signal 507 from the memory 405 in the second signal processing unit and target position information and probe position information from the system control unit 401. On the basis of the received target position information and probe position information when the scan line signals are acquired, delay processing is performed on the scan line signals. In the delay processing, a delay time is calculated with reference to the period of time from the transmission of ultrasound from a probe position to the return to the original probe position through the target position (or with reference to the time required for the round trip). Hilbert transform is performed on the scan line signals, and signals in complex representation are output.

In this way, the scan line signals having undergone the delay processing are input to a partial correlation matrix calculating circuit 407. The partial correlation matrix calculating circuit 407 extracts signals for the number of samples (such as for 10 samples) required for calculating a correlation matrix from the input scan line signal, generates a correlation matrix, and averages the submatrices to calculate the average correlation matrix. The partial correlation matrix calculating circuit 407 continuously calculates an average correlation matrix for the input scan line signal. In other words, the average correlation matrix is updated and is output with a change in scan line signal.

A weight calculating circuit 408 calculates the inverse matrix of the input average correlation matrix and uses a constrained vector input from the system control unit 401 as required to calculate a weight. The weight changes in accordance with the update of the average correlation matrix. A synthesized scan line signal calculating circuit 409 a scan line signal and the weight calculated from the scan line signal to calculate the synthesized scan line signal (second output signal) and outputs it to the signal filter circuit 411.

In this way, the second signal processing unit applies adaptive signal processing to calculate and output a synthesized scan line signal. A signal filter circuit 411 may perform processing such as band-pass filtering, for example, on the input synthesized scan line signal as required and acquires an envelope of the signal. In accordance with an instruction from the system control unit, the signal filter circuit 411 outputs a log-compressed signal intensity. An image processing unit 412 may perform image filtering (such as edge emphasis and smoothing) as required and further performs the processing according to the display method (such as cross-section slice display and 3D rendering) instructed by the system control unit 401 to generate three-dimensional image data for display. The three-dimensional image data is transmitted to an image display device 413, and the image display device 413 displays the three-dimensional image.

Figure 6:
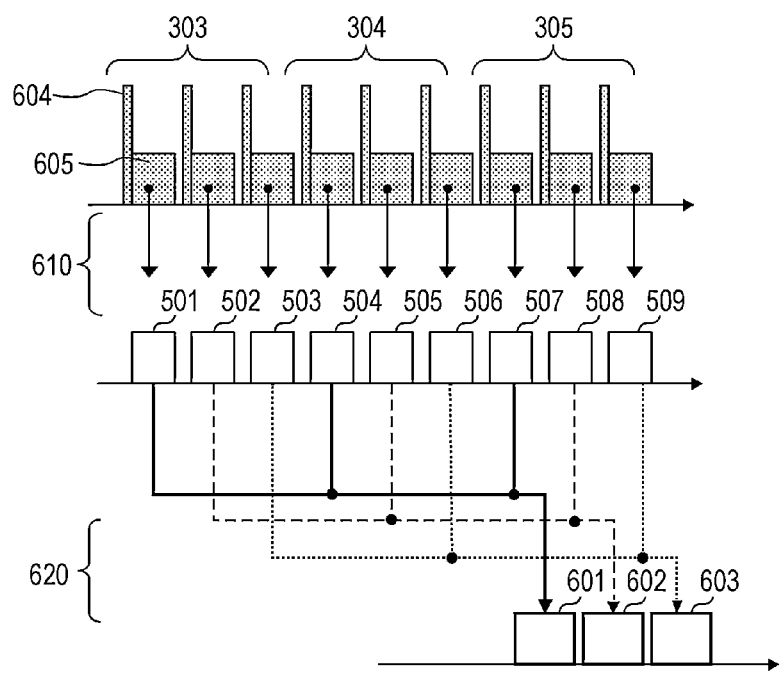
FIG. 6 is a schematic diagram illustrating scan line signal acquisition timing and operation timing by a second signal processing unit.

FIG. 6 is a schematic diagram illustrating a relationship between scan line signal acquisition timing and operation timing by the second signal processing unit 420. The upper part of FIG. 6 illustrates ultrasound transmission and reception processing timing to be performed when the probe 302 is at the positions 303, 304, and 305. According to this embodiment, a transmission processing timing 604 and a reception processing timing 605 are repeated. In each of the reception processing timing 605, the first signal processing unit performs signal processing (delay and sum) 610 according to this embodiment to calculate scan line signals 501 to 509, which are then stored in a memory. When the scan line signals 501, 504, and 507 are provided, the second signal processing unit starts signal processing (adaptive signal processing according to this embodiment) 620 by the second signal processing unit and outputs the synthesized scan line signal 601. When the scan line signals 502, 505, and 508 are provided, the next processing is started, and the synthesized scan line signal 602 is output. In this way, the second signal processing unit starts the processing for calculating a synthesized scan line signal when a required scan line signal is provided.

Figure 7A:
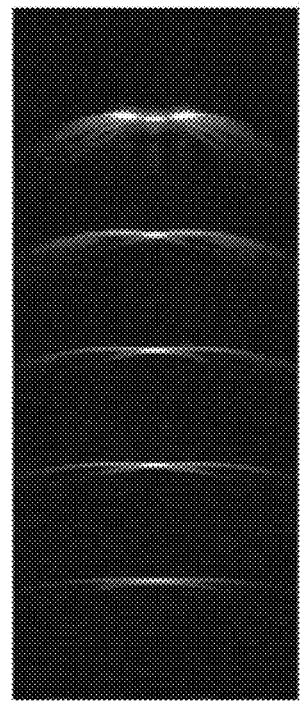
FIG. 7A is a simulation result of an image.
Figure 7B:
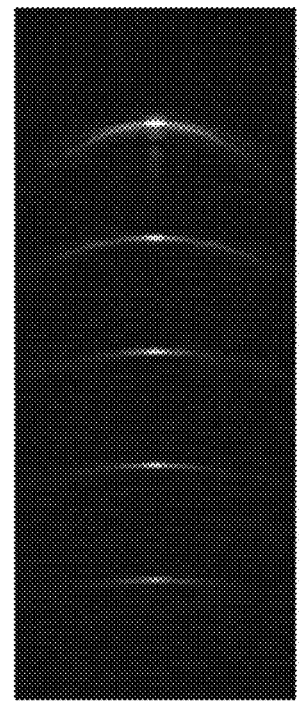
FIG. 7B is a simulation result of an image.

FIGS. 7A and 7B illustrate images as a result of the simulation of a case where five wires in parallel with the array direction of a one-dimensional array probe. FIGS. 7A and 7B are cross-section views including the direction of the mechanical scan and the direction of depth to be observed. FIG. 7A illustrates an image as a result of delay and sum in the array direction and synthesized aperture processing in the direction of mechanical scan. FIG. 7B illustrates an image as a result of delay and sum in the first signal processing unit and adaptive signal processing in the second signal processing unit according to this embodiment. The spatial resolution is improved on the image in FIG. 7B as a result of the processing of this embodiment.

In this way, according to this embodiment, the application of adaptive signal processing in the second signal processing unit may provide an apparatus which may reduce the size of the adaptive signal processing and particularly provide a high spatial resolution in the direction of mechanical scan.

According to this embodiment, a probe is moved by mechanical scan. However, positional information where scan line signals are acquired is grasped with a position sensor or by image processing. Thus, the present invention is applicable to a probe which moves freely, providing an improved spatial resolution.

Compared with the case where a probe moves freely, when a probe scans mechanically by using a stage, the relative positions between positions where scan line signals are acquired and a target position may be grasped accurately. This allows delay processing circuit with high precision and may provide a higher spatial resolution.

According to this embodiment, the probe stays still at the positions 303, 304, and 305 to acquire data. In reality, however, signal processing may be performed in the same manner even when the probe moves continuously, and the same effect can be provided.

Second Embodiment

According to this embodiment, a one-dimensional array probe scans mechanically, and, at the same time, both first signal processing unit and second signal processing unit use adaptive signal processing.

Since scan timing and operation timing by the first signal processing unit and second signal processing unit are the same, the descriptions will be omitted. The signal processing part will only be described.

Figure 8:
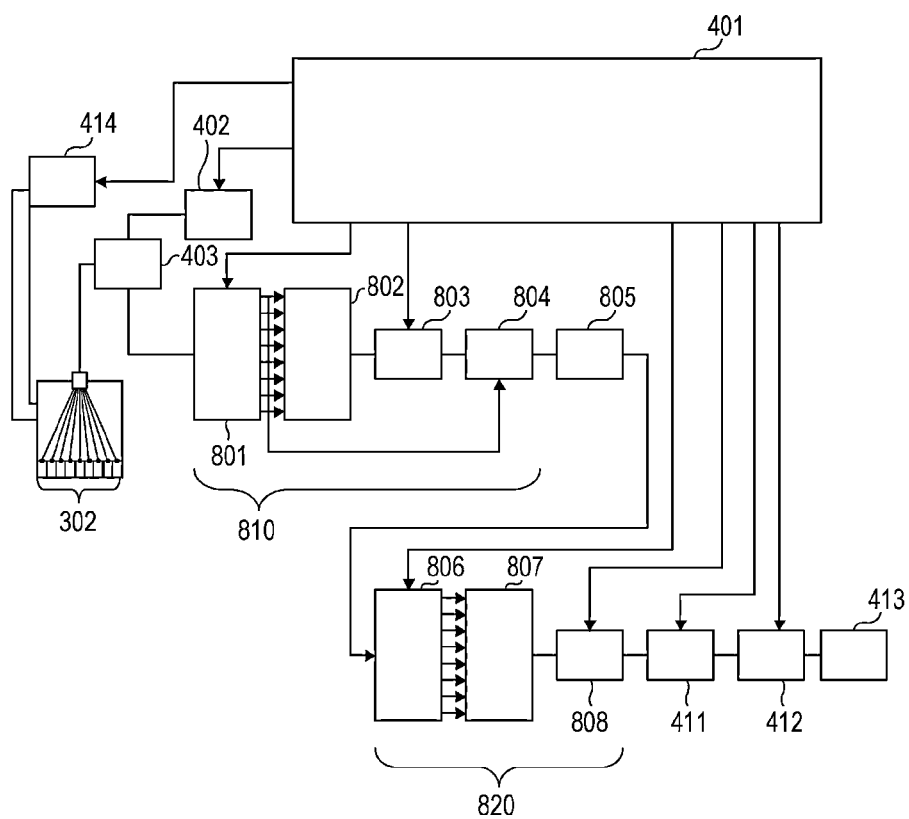
FIG. 8 is a schematic system diagram illustrating a second embodiment.

FIG. 8 is schematic system diagram of an apparatus according to this embodiment. First of all, a transmission operation will be described. In a transmission operation, information according to the direction of transmission is input from the system control unit 401 to the transmitting circuit 402. The transmitting circuit 402 calculates a delay time according to the array of elements of the probe and outputs a voltage waveform to the switching circuit 403. The switching circuit 403 selectively connects elements in the part to be used of the probe 302 and the transmitting circuit 402. For linear scan, for example, serial 64 elements of the array of elements of the 256 CH are selected and connected to the transmitting circuit 402. Ultrasound is transmitted from the probe 302 to the inside of a subject.

Next, an operation by the first signal processing unit by using adaptive signal processing will be described. The ultrasound reflected in accordance with the acoustic impedance distribution within the subject is converted by an ultrasound converter to a received signal which is an electric signal. After that, the received signal is input through the switching circuit 403 to the first signal processing unit 810. A delay processing circuit 801 in the first signal processing unit receives a received signal from an element and also receives target position information from the system control unit 401. The delay processing circuit 801 uses the input target position information to perform delay processing to equalize the phases of the received signals corresponding to the ultrasound from a target position. Hilbert transform is performed on the scan line signals, and signals in complex representation are output.

The partial correlation matrix calculating circuit 802 extracts signals for the number of samples required for calculating a correlation matrix from the input scan line signal, generates a correlation matrix, and averages the submatrices to calculate the average correlation matrix. The partial correlation matrix calculating circuit 802 continuously calculates an average correlation matrix for the input received signals. In other words, the average correlation matrix is updated and is output with a change in received signal.

A weight calculating circuit 803 calculates the inverse matrix of the input average correlation matrix and uses a constrained vector input from the system control unit 401 as required to calculate a weight. The weight changes in accordance with the update of the average correlation matrix.

The scan line signal calculating circuit 804 uses the input received signal and the weight calculated from the received signal to calculate an output signal and outputs it as a scan line signal (first output signal). The resulting scan line signal here holds the phase of the received signal from a target position, as described above. The output scan line signal is stored in the memory 805.

After that, the switching circuit 403 is switched, scan line signals are acquired from a plurality of different positions by the operation for changing the element to be used in the array direction and the movement of the probe and are stored in the memory 805. The operation is the same as Embodiment 1.

Next, second signal processing unit will be described. A second signal processing unit 820 starts processing when scan line signals required for the processing are provided. A delay processing circuit 806 in the second signal processing unit receives a scan line signal from the memory 405, target position information from the system control unit 401, and positional information on the probe. Delay processing is performed on a scan line signal from the input target position information and positional information on the probe when the scan line signal is acquired obtained. The phasing-delayed scan line signal is input to a partial correlation matrix calculating circuit 807.

The partial correlation matrix calculating circuit 807 extracts signals for the number of samples required for calculating a correlation matrix from the input scan line signal, generates a correlation matrix, and averages the submatrices to calculate the average correlation matrix. The partial correlation matrix calculating circuit 807 continuously calculates an average correlation matrix for the input scan line signal. In other words, the average correlation matrix is updated and is output with a change in scan line signal.

A synthesized scan line power calculating circuit 808 calculates the inverse matrix of the input average correlation matrix and uses a constrained vector input from the system control unit 401 as required to calculate a weight. The synthesized scan line power is output as the second output signal. The second output signal is the synthesized scan line power (without positive/negative value, only positive value). The synthesized scan line power changes in accordance with the update of the average correlation matrix.

In this way, the synthesized scan line power is calculated by the second signal processing unit and is output to the signal filter circuit 411. For the input synthesized scan line power, the signal filter circuit 411 outputs a log-compressed signal intensity in accordance with an instruction from the system control unit 401. The image processing unit 412 may perform image filtering (such as edge emphasis and smoothing) as required and further performs the processing corresponding to the display method (such as cross-section slice display and 3D rendering) instructed by the system control unit 401 to generate three-dimensional image data for display. The image display device 413 displays a three-dimensional image on the basis of the three-dimensional image data transmitted from the image processing unit 412.

According to this embodiment, the second signal processing unit calculates direct power from the average correlation matrix. In this way, the output of the second signal processing unit may not be required to hold the phase of the signal corresponding to the ultrasound from a target position. Therefore, direct power may be calculated and be output.

According to this embodiment, the first signal processing unit and second signal processing unit applies adaptive signal processing. The output of the first signal processing unit is calculated by acquiring the inner product of a weight which can hold the phase of the signal corresponding to the ultrasound from a target position and the received signal. Thus, second signal processing unit may be allowed to apply adaptive signal processing. Therefore, there may be provided an apparatus which can reduce the size of signal processing and has a high spatial resolution in the direction of the element array and the direction of the mechanical scan.

According to this embodiment, the first signal processing unit and second signal processing unit applies adaptive signal processing. However, the second signal processing unit may apply synthesized aperture processing including delay processing and sum processing by acquiring the output of the first signal processing unit on the basis of the inner product of a weight which can hold the phase of an ultrasonic signal from a target position and the received signal. In this case, there may be provided an apparatus which has a high spatial resolution in the array direction.

Even when a two-dimensional array probe is used, the effect of the present invention may be provided by the calculation of the scan line signal by the first signal processing unit.

Third Embodiment

The present invention may be implemented by execution of the following processing. That is, software (program) which implements the functions of the aforementioned embodiments is supplied to a system or apparatus through a network or a storage medium. A computer (such as a CPU or an MPU) in the system or apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-207894, filed Sep. 16, 2010, which is hereby incorporated by reference herein in its entirety.

REFERENCE SIGNS LIST

10 First Signal Processing Unit
20 Second Signal Processing Unit
101 Delay processing circuit
102 Averaged Correlation Matrix Calculating Circuit
103 Weight Calculating Circuit
104 First Output Calculating Circuit
105 Memory
106 Delay processing circuit
107 Averaged Correlation Matrix Calculating Circuit
108 Weight Calculating Circuit
109 Second Output Calculating Circuit
301 Element
302 Probe
401 System Control Unit
402 Transmitting Circuit
403 Switching Circuit
404 Delay and sum processing circuit
405 Memory
406 Delay processing circuit
407 Partial Correlation Matrix Calculating Circuit
408 Weight Calculating Circuit
409 Synthesized Scan Line Signal Calculating Circuit
410 First Signal Processing Unit
411 Signal Filter Circuit
412 Image Processing Unit
413 Image Display Device
414 Stage Control Circuit
420 Second Signal Processing Unit
501 To 509 Scan Line Signal
601, 602, 603 Synthesized Scan Line Signal

The invention claimed is:

1. A subject information acquiring apparatus comprising:
a probe having a plurality of elements arranged in a first direction, each of the elements configured to receive an elastic wave propagating within a subject and convert the received elastic wave to a received signal;
a stage configured to move the probe in a second direction;
a first signal processing unit configured to calculate first output signals using a plurality of received signals output by the elements, each of the first output signals corresponding to different elastic waves from different target positions within the subject, wherein the first output signals include phase information of the elastic waves from the different target positions;
a second signal processing unit configured to calculate a second output signal using a plurality of the first output signals corresponding to different elastic waves from target positions mutually different in the second direction within the subject; and
an image processing unit configured to generate image data for display using the second output signal,
wherein at least one of the first signal processing unit and the second signal processing unit uses adaptive signal processing to calculate the first output signal or the second output signal.

2. The subject information acquiring apparatus according to claim 1, wherein:
the first signal processing unit uses a weight calculated by adaptive signal processing and the received signals by the elements to calculate the first output signal for the target position, and
the second signal processing unit uses the first output signal for the target position to perform synthesized aperture processing and calculate the second output signal.

3. The subject information acquiring apparatus according to claim 1, wherein:
the first signal processing unit uses the received signals by the elements to perform delay and sum and calculate the first output signal for the target position; and
the second signal processing unit uses the first output signal for the target position to perform adaptive signal processing and calculate the second output signal.

4. The subject information acquiring apparatus according to claim 1, wherein:
the first signal processing unit uses a weight calculated by adaptive signal processing and the received signals by the elements to calculate the first output signal for the target position; and
the second signal processing unit uses the first output signal for the target position to perform adaptive signal processing and calculate the second output signal.

5. The subject information acquiring apparatus according to claim 1, further comprising a stage configured to move the probe.

6. The subject information acquiring apparatus according to claim 1, wherein the second signal processing unit begins the calculation of the second output signal when the first output signals for a target position are provided.

7. A subject information acquiring method for receiving elastic waves propagating within the subject with a plurality of elements arranged in a first direction, converting the received elastic waves to received signals, and using the received signals to generate image data, the method comprising:
a moving step for moving the plurality of elements in a second direction;
a first signal processing step for calculating first output signals, using the received signals output by the elements, each of the first output signals corresponding to different elastic waves from different target positions within the subject, wherein the first output signals include phase information of the elastic waves from the different target positions;
a second signal processing step for calculating a second output signal using the first output signals corresponding to different elastic waves from target positions mutually different in the second direction within the subject; and
an image processing step for generating image data for display using the second output signal,
wherein at least one of the first signal processing step and the second signal processing step uses adaptive signal processing to calculate the first output signal or the second output signal.

8. The subject information acquiring method according to claim 7, wherein:
the first signal processing step uses a weight calculated by adaptive signal processing and the received signals by the elements to calculate the first output signal for the target position, and
the second signal processing step uses the first output signal for the target position to perform synthesized aperture processing and calculate the second output signal.

9. The subject information acquiring method according to claim 7, wherein:

the first signal processing step uses the received signals by the elements to perform delay and sum and calculate the first output signal for the target position; and the second signal processing step uses the first output signal for the target position to perform adaptive signal processing and calculate the second output signal.

10. The subject information acquiring method according to claim 7, wherein:

the first signal processing step uses a weight calculated by adaptive signal processing and the received signals by the elements to calculate the first output signal for the target position; and the second signal processing step uses the first output signal for the target position to perform adaptive signal processing and calculate the second output signal.

11. A program for causing a computer to execute the subject information acquiring method according to claim 7.

12. The subject information acquiring method according to claim 7, wherein in the second signal processing step, the calculation of the second output signal begins when the first output signals for a target position are provided.

* * * * *